US006306345B1

(12) United States Patent
Bronshtein et al.

(10) Patent No.: US 6,306,345 B1
(45) Date of Patent: Oct. 23, 2001

(54) INDUSTRIAL SCALE BARRIER TECHNOLOGY FOR PRESERVATION OF SENSITIVE BIOLOGICAL MATERIALS AT AMBIENT TEMPERATURES

(75) Inventors: Victor Bronshtein, San Diego; Kevin R. Bracken, Poway; Ronnie K. Livers, San Diego; David R. Williams, Temecula, all of CA (US)

(73) Assignee: Universal Preservation Technologies, Inc., San Diego, CA (US)

( * ) Notice: Subject to any disclaimer, the term of this patent is extended or adjusted under 35 U.S.C. 154(b) by 0 days.

(21) Appl. No.: 09/306,137

(22) Filed: May 6, 1999

Related U.S. Application Data

(60) Provisional application No. 60/084,451, filed on May 6, 1998, provisional application No. 60/114,774, filed on Jan. 5, 1999, and provisional application No. 60/114,775, filed on Jan. 5, 1999.

(51) Int. Cl.[7] .................. B01J 19/00

(52) U.S. Cl. .................. 422/41; 422/1; 422/41; 422/309; 252/501; 252/528; 435/243

(58) Field of Search .................. 34/92, 145, 381, 34/387, 406, 1, 41; 422/309; 252/501, 528; 435/243

(56) References Cited

U.S. PATENT DOCUMENTS

| | | | | |
|---|---|---|---|---|
| 5,098,893 | | 3/1992 | Franks et al. . | |
| 5,257,466 | * | 11/1993 | Kishi | 34/95 |
| 5,334,621 | * | 8/1994 | Beshouri | 521/64 |
| 5,428,906 | * | 7/1995 | Lynam et al. | 34/379 |
| 5,593,824 | * | 1/1997 | Treml et al. | 435/4 |
| 5,662,279 | * | 9/1997 | Czekai et al. | 241/21 |
| 5,707,634 | * | 1/1998 | Schmitt | 424/400 |

FOREIGN PATENT DOCUMENTS

| | | |
|---|---|---|
| WO 96/40077 | 12/1996 | (WO) . |
| WO 98/02240 | 1/1998 | (WO) . |
| WO 99/27071 | 6/1999 | (WO) . |

* cited by examiner

*Primary Examiner*—Robert J. Warden, Sr.
*Assistant Examiner*—Imad Soubra
(74) *Attorney, Agent, or Firm*—Knobbe, Martens, Olson & Bear LLP

(57) ABSTRACT

This invention relates to barrier methods for preserving sensitive biological materials as a porous foam, subsequently crushing the foam to form a powder, and optionally formulating mixtures of preserved powdered biological materials. The invention also encompasses an apparatus for integrating the methods of foam formation and subsequent crushing of the preserved biological materials using barrier technology.

47 Claims, 2 Drawing Sheets

INDUSTRIAL SCALE BARRIER TECHNOLOGY FOR PRESERVATION OF SENSITIVE BIOLOGICAL MATERIALS AT AMBIENT TEMPERATURES

RELATED APPLICATIONS

This application claims priority under 35 U.S.C. §119(e) to Provisional Application No. 60/084,451, filed May 6, 1998, Provisional Application No. 60/114,774, filed on Jan. 5, 1999 and Provisional Application No. 60/114,775, filed on Jan. 5, 1999.

BACKGROUND OF THE INVENTION

1. Field of the Invention

This invention relates to preservation of sensitive biological materials in the form of dehydrated powder stored at temperatures above 0° C. More particularly, the invention relates to a technological process for integrating the following steps: preservation of the biological materials by foam formation, subsequent drying and milling of the foam to form a dry powder, and formulation of mixed dry powder product (cereals) for different practical applications.

2. Description of the Related Art

The preservation and storage of solutions or suspensions of biologically active materials, viruses, cells and small multicellular specimens is important for food and microbiological industries, agriculture, medical and research purposes. Storage of these dehydrated biologically active materials carries enormous benefits, such as reduced weight and reduced storage space, and increased stability.

Suggestions in the prior art for providing preservation of sensitive biological materials in dehydrated form include freeze-drying and vacuum or air-desiccation. Both, freeze-drying and desiccation preservation methods have positive and negative characteristics. While freeze-drying methods are scaleable to industrial quantities, conventional vacuum and air-desiccation methods do not yield preparations of biological materials which are scalable to industrial quantities. Freezing and other steps of the freeze-drying process are very damaging to many sensitive biological materials. The freeze-drying process is very long, cost ineffective, and cannot be performed using barrier technology to ensure sterility of the material.

Some of the problems associated with preservation by freezing and drying have been addressed by addition of protectant molecules, especially carbohydrates, which have been found to stabilize biological materials against the stresses of freezing and drying. However, despite the presence of protectants, the long-term stability after freeze-drying may still require low temperature storage, in order to inhibit diffusion-dependent destructive chemical reactions. Thus, further innovations have been sought to provide long-term storage of labile biological materials at ambient temperatures.

Storage of dried materials at ambient temperatures would be cost effective when compared to low temperature storage options. Furthermore, ambient temperature storage of biological materials such as vaccines and hormones would be extremely valuable in bringing modem medical treatments to third world countries where refrigeration is often unavailable. As the many benefits of shelf preservation of biological specimens have come to be appreciated, researchers have endeavored to harness vitrification as a means of protecting biological materials against degradative processes during long-term storage. Consequently, this technology of achieving the "glass" state has been anticipated to emerge as a premier preservation technique for the future.

A glass is an amorphous solid state that may be obtained by substantial undercooling of a material that was initially in the liquid state. Diffusion in vitrified materials, or glasses, occurs at extremely low rates (e.g. microns/year). Consequently, chemical or biological changes requiring the interaction of more than one moiety are practically completely inhibited. Glasses normally appear as homogeneous, transparent, brittle solids, which can be ground or milled into a powder. Above a temperature known as the glass transition temperature (Tg), the viscosity drops rapidly and the glass becomes deformable and the material turns into a fluid at even higher temperatures. The optimal benefits of vitrification for long-term storage may be secured only under conditions where Tg is greater than the storage temperature. The Tg is directly dependent on the amount of water present, and may therefore be modified by controlling the level of hydration; the less water, the higher the Tg.

Unfortunately, the advantages of vitrification technology as a means of conferring long-term stability to labile biological materials at ambient temperatures has not been fully utilized. Conventional methods of ambient temperature preservation by dessication are designed for laboratory processing of very small quantities of materials. Recently, V. Bronshtein developed an alternative method of preservation by foam formation (U.S. Pat. No. 5,766,520) that is compatible with large-scale commercial operations. Preservation by foam formation overcomes the technical problems related to scaling up desiccation and vitrification preservation processes. For this reason, preservation by foam formation is attractive as a scalable method for long-term storage of biological materials.

The present invention solves instrumentation problems related to preservation by foam formation and processing operations. Specially designed devices and instruments must be employed to reproducibly produce a dehydrated, shelf-stable, foams and uniform powder of the preserved materials. The instruments should integrate the ability to execute a barrier scalable preservation of biological material by desiccation, subsequent transformation of the dry material into powder form (for example by milling) and usage of dry powders to formulate products that may contain mixtures of different biological materials.

SUMMARY OF THE INVENTION

The present invention relates to a barrier method for preserving a biological solution or suspension as a foam or powder. The method comprises the following steps: drying the biological solution or suspension in a chamber at non-damaging temperatures by first boiling the sample under vacuum to form a mechanically stable foam, second dehydrating the foams at elevated temperature to obtain the glass transition temperature required to insure stability of preserved materials during storage, and crushing (and/or milling) the mechanically stable foam to form a powder.

The method further provides that the biological solution or suspension may be combined with a protectant prior to drying. Similar to other methods of preservation in the dry state, sugars, polyols and their polymers can be used to protect the material from the damaging effect of desiccation. More specifically, the protectant comprises a mixture comprising a monosaccharide, a disaccharide, and a polymer. The monosaccharide may be selected from the group consisting of non-reducing derivatives of fructose, glucose, sorbose, piscose, ribulose, xylulose, erythulose, and the like.

Such derivatives may be obtained by methylating, ethylating, chlorinating or otherwise modifying the reducing groups.

Prior to milling the foams it may optionally be further dried under conditions sufficient to increase its stability at a desired storage temperature. The increased stability obtained during this secondary drying procedure may be performed inside the drying chamber or outside the drying chamber during warehouse storage. Alternatively, the foam may be further dried under conditions sufficient to increase its glass transition temperature above a desired storage temperature. These further drying steps may be applied after the foam has been crushed to form a powder.

A means for crushing the foam may be incorporated into the chamber. The crushing means may comprise a mill selected from the group consisting of a brush mill, a rotating blade mill, a pulverizing mill, a rotary attrition mill, a jet mill, an incremental cutting action mill, a ball mill, a hammer mill, a rotary tubular mill, a homogenizer, and a sonicator. Alternatively, the crushing means may comprise a deformable container inside the chamber, wherein the drying step is conducted inside of the deformable container. Where drying is conducted in a deformable container, crushing may be accomplished by mechanically deforming the deformable container. To maintain sterility, consistent with barrier technology, the deformable container may be sealed prior to deforming the container.

A variation of the deformable container of the present invention is a gas-permeable container, to allow dying of the biological solution or suspension, while maintaining sterility and holding the liquid or foam. The deformable container may also be semirigid.

Another variation of the method involves a tray inside the chamber. The tray may be subdivided by a grid, which may hold the solution or suspension or support a flexible deformable container such as a bag.

An apparatus for preserving and crushing a biological sample is also disclosed comprising a chamber having a means for regulating chamber temperature, a means for regulating chamber pressure, and a means for crushing mechanically stable foam. The process chamber may be sized to accommodate different volumes of biological solutions or suspensions ranging from at least 1 liter, to at least 10 liters, up to at least 100 liters.

The means for regulating chamber temperature is capable of producing a chamber temperature within a range of approximately −70° to 300° C. The means for regulating pressure is capable of producing a chamber pressure within a range of approximately 0.01 to about 500 Torr. The means for crushing may comprise a mill or a deformable container (bag), inside the chamber. The mill may be selected from the group consisting of a brush mill, a rotating blade mill, a pulverizing mill, a rotary attrition mill, a jet mill, an incremental cutting action mill, a ball mill, a hammer mill, a rotary tubular mill, a homogenizer, and a sonicator.

Preferably, the apparatus will have sensors for detecting chamber temperature and pressure, as well as a programmable computer adapted to monitor and control chamber temperature and pressure.

The dry powders may be stored under dry conditions. The final product can be formulated in a variety of different ways, such as by mixing one or more powders and placing the mixture in vials or other containers that can be sealed, by preparing tablets by pressing the powders, or by preparing devices for powder inhalation, internasal or other ways of dry material delivery.

DETAILED DESCRIPTION OF THE PREFERRED EMBODIMENT

Figure 1:
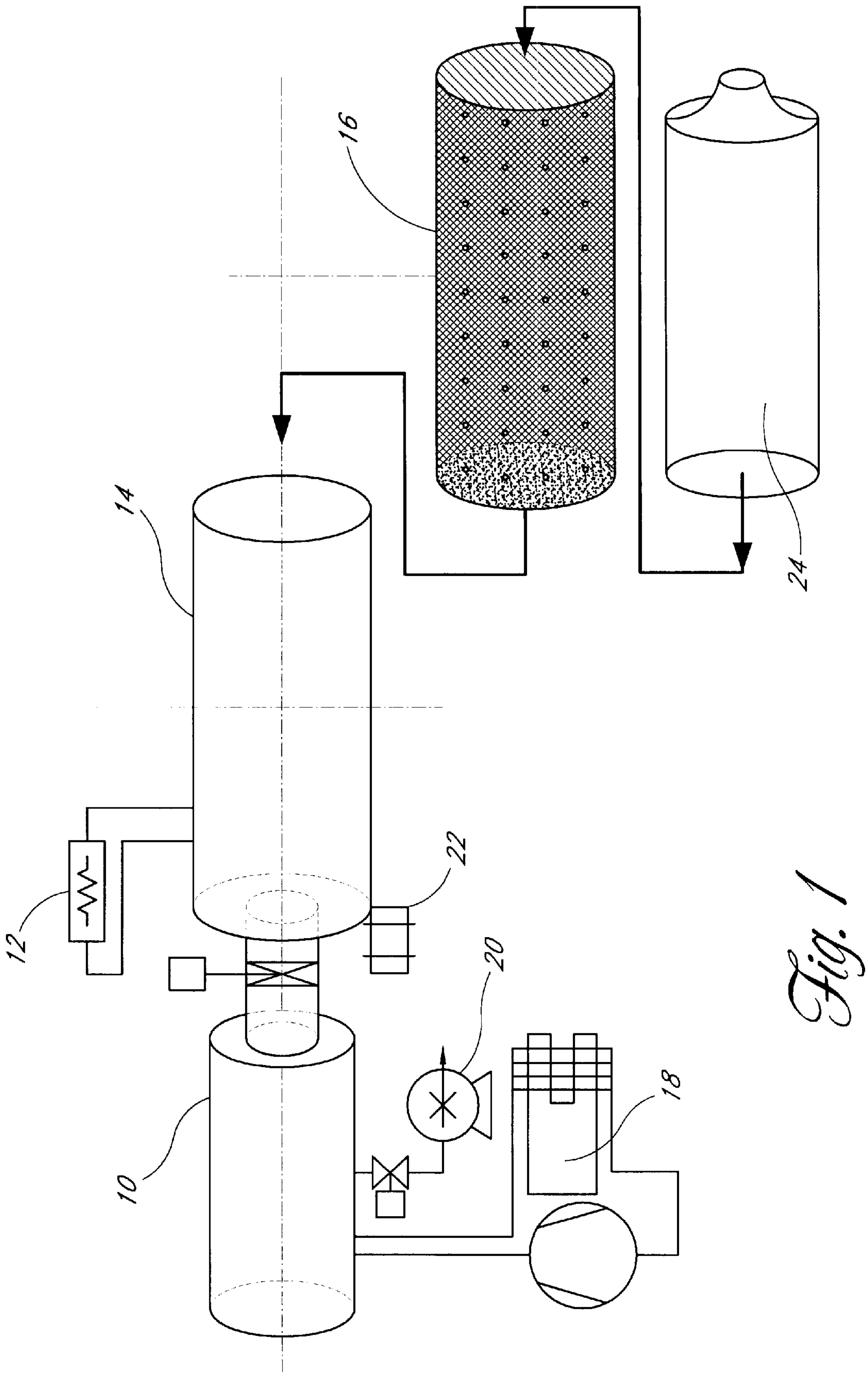
FIG. 1 is a schematic drawing of an integrated apparatus for foam-drying in a deformable bag according to one embodiment of the present invention.

The present invention discloses a combination of preservation and processing methods for application to biologically active materials. The methods may be carried out using barrier technology to protect the sterility of the biological materials in an integrated processing chamber, designed to facilitate the various methodological operations. Features and limitations of the methods and apparatus are described separately herein for the purpose of clarity.

Biological Materials—Biologically active materials which can be preserved by the present methods include, without limitation, biological solutions and suspensions containing peptides, proteins, antibodies, enzymes, co-enzymes, vitamins, serums, vaccines, viruses, liposomes, cells and certain small multicellular specimens. Dehydration of biological specimens at elevated temperatures may be very damaging, particularly for example, when the temperatures employed for drying are higher than the applicable protein denaturation temperature. To protect the samples from the damage associated with elevated temperatures, the dehydration process may be performed in steps or by simultaneous increase in temperature and extent of dehydration. Primary dehydration should be performed at temperatures that are sufficiently low to permit dehydration without loss of biological activity.

Protectants (fillers)—A variety of polyols and polymers are known in the art and may serve as protectants as long as they enhance the ability of the biologically active material to withstand drying and storage and do not interfere with the particular biological activity. Indeed, the protectant molecules provide other advantages during preservation (see infra, as an aid to generating mechanically stable foams) besides stabilizing biological materials during dehydration. More particularly, the protectants in accordance with the present invention may include, without limitation, simple sugars, such as sucrose, glucose, maltose, sucrose, xylulose, ribose, mannose, fructose, raffinose, and trehalose, non-reducing derivatives of monosaccharides and other carbohydrate derivatives, sugar alcohols like sorbitol, synthetic polymers, such as polyethylene glycol, hydroxyethyl starch, polyvinyl pyrrolidone, polyacrylamide, and polyethyleneamine, and sugar copolymers, like Ficoll and Dextran, and combinations thereof. Low molecular weight, highly soluble proteins may also serve as protectants.

In a variation of the present invention, where cells or viruses are being preserved, the protective composition may further comprise mixtures of a low molecular weight sugar, a disaccharide, oligosaccharide and polymer including biological polymer. The low molecular weight sugar is used to penetrate and protect intracellular structures during dehydration. The low molecular weight, permeating sugars may be selected from a variety of ketoses, which are non-reducing at neutral or higher pH, or methylated or ethylated monosaccharides. Among the non-reducing ketoses, are included: the six carbon sugars, fructose, sorbose, and piscose; the five carbon sugars, ribulose and xylulose; the four-carbon sugar, erythulose; and the three-carbon sugar, 1,3 dihydroxydimethylketone. Among the methylated monosaccharides, are the alpha and beta methylated forms of gluco, manno, and galacto pyranoside. Among the methylated five carbon compounds are the alpha and beta forms of arabino and xylo pyranosides. Disaccharides, like sucrose, are known to be effective protectants during desiccation because they replace the water of hydration on the surface of biological membranes and macromolecules. In addition, the Inventor has found that when dried under vacuum, sucrose and/or other fillers may be effectively transformed into a stable foam, composed of thin amorphous films of the concentrated sugar.

The Inventor has also found that combining monosaccharides with disaccharides and oligosaccharides effectively prevents crystallization of the oligosaccharides during dehydration. Finally, a polymer may be employed to increase the glass transition temperatue (Tg) of the dehydrated mixture, which may be decreased by inclusion of the low molecular weight monosaccharides. Any biological polymers that are highly soluble in concentrated sugar solutions may be employed. For example, polysaccharides, like Ficoll, and Dextran, and synthetic polymers, like hydroxyethyl starch, polyethylene glycol, polyvinyl pyrrolidone, polyacrylamide, as well as highly soluble natural and synthetic biopolymers (e.g. proteins) will help to stabilize biological membranes and increase Tg.

Primary Foam-Drying—To facilitate scale-up of the processing operations, preservation by foam formation involves the formation of a mechanically stable porous structure by boiling under a vacuum. The drying step is carried out at temperatures in the range of about −15° to 70° C. The mechanically stable porous structure, or foam, consists of thin amorphous films of the concentrated fillers. Preservation by foam formation is particularly well suited for efficient drying of large sample volumes, before vitrification, and as an aid in preparing a readily milled dried product suitable for commercial use. Further details of preservation by foam formation are included in U.S. Pat. No. 5,766,520 by Bronshtein; incorporated herein in its entirety by reference thereto.

In a variation of the present invention, dilute biological samples may be concentrated by partially removing the water to form a viscous specimen before foam-drying under vacuum. This initial concentration step can be accomplished either before or after introduction of the sample into the processing chamber, depending on the concentration method chosen. Alternatively, some samples may be sufficiently viscous after addition of the protectant molecules, and therefore not require any initial concentration. In situations where it is desirable to increase the viscosity of the samples, methods contemplated for use in initial concentration include freeze-drying, evaporation from liquid or partially frozen state, reverse osmosis, other membrane technologies, or any other concentration methods known in the art.

The viscous samples are subjected to vacuum, to cause them to boil during drying at temperatures substantially lower than 100° C. In other words, reduced pressure is applied to viscous solutions or suspensions of biologically active materials to cause the solutions or suspensions to foam during boiling, and during the foaming process further solvent removal causes the ultimate production of a mechanically-stable open-cell or closed-cell porous foam.

While low vacuum pressures (in the range of 0.1–0.9 atm) may be applied to facilitate the initial evaporation to produce a concentrated, viscous solution, much higher vacuum pressures (0–24 Torr) are used to cause boiling. The vacuum for the boiling step is preferably 0–10 Torr, and most preferably less than about 4 Torr. Boiling in this context means nucleation and growth of bubbles containing water vapor, not air or other gases. In fact, in some solutions, it may be advantageous to purge dissolved gases by application of low vacuum (about 0.1–0.9 atm) at room temperature. Such "degassing" may help to prevent the solution from erupting out of the drying vessel. Once the solution is sufficiently concentrated and viscous, high vacuum can be applied to cause controlled boiling or foaming. Concentration of the protectant molecules recited above, in the range of 5–70% by weight, during initial evaporation aids in preventing freezing under subsequent high vacuum and adds to the viscosity, thereby facilitating foaming while limiting uncontrolled eruptions.

Rapid increases in pressure or temperature could cause a foam to collapse. In this case, to enhance the mechanical stability of the porous structures, surfactants may be added as long as those additives do not interfere with the biological activity of the solute intended for conversion to dry form. Moreover, drying of the protectant polymers also contributes to the mechanical stability of the porous structures. Foams prepared according to the present invention may be stored in the processing chamber under vacuum, dry gas, like $N_2$ atmosphere and/or chemical desiccant, prior to subsequent processing operations, (e.g. stability drying, vitrification or milling).

The following working examples illustrate formation of the mechanically stable porous foam in accordance with the process of preservation by foam formation:

(1) An aqueous 50% glycerol isocitrate dehydrogenase solution from Sigma Chemical Co. containing 59.4 units of activity per ml was dialyzed for 5 hours in 0.1 M TRIS HCl buffer (pH 7.4). The activity of the isocitrate dehydrogenase in the 0.1 M TRIS HCl solution after dialysis was 26±1.8 units per ml. The activity decrease was associated with a decrease in the enzyme concentration because of dilution during the dialysis.

A mixture (100 μl) containing 50 μl of 50% by weight sucrose solution and 50 μl of the isocitrate dehydrogenase suspension in 0.1 M TRIS HCl buffer (pH 7.4) was placed in 1.5 ml plastic tubes and preserved by drying at room temperature. First, the samples were dried for 4 hours under low vacuum (0.2 atm). Second, the samples were boiled during 4 hours under high vacuum (<0.01 atm). During this step, a mechanically stable dry foam was formed in the tubes. Third, the samples were stored during 8 days over DRIERITE under vacuum at room temperature.

After 8 days, the samples were rehydrated with 500 μl water. Rehydration of the samples containing dry foams was an easy process that was completed within several seconds. The reconstituted sample was assayed for activity by assaying ability to reduce NADP, measured spectrophotometrically at 340 nm. The reaction mix included: 2 ml 0.1 M TRIS HCl buffer, pH 7.4; 10 μl of 0.5% by weight NADP+; 10 μl of 10 mM $MnSO_4$; 10 μl of 50 mM 1-isocitrate; and 10 μl of an isocitrate dehydrogenase solution. The activity was 2.6±0.2 units/ml, which means there was no loss of activity during drying and subsequent storage at room temperature.

(2) A mixture (100 μl) containing 50 μl of 50% by weight sucrose and 50 μl of an ice nucleating bacteria suspension, (INB) Pseudomonas Syringae ATCC 53543, were placed in 1.5 ml plastic tubes and preserved by drying at room temperature. First, the samples were dried for 4 hours under low vacuum (0.2 atm). Second, the samples were boiled during 4 hours under high vacuum (<0.01 atm). After boiling under high vacuum, a mechanically-stable porous structure was formed. Third, the samples were stored during 8 days over DRIERITE under vacuum at room temperature.

After 8 days, the samples were rehydrated with 500 $\mu$l water. Rehydration of the samples containing the dry foams was an easy process that was completed within several seconds. Then the samples were assayed for ice nucleation activity in comparison with control samples. There was no significant difference between the ice nucleating activity per 1,000 bacteria in the samples preserved by the present method versus the control samples.

(3) A sample containing a 1:1 mixture of a concentrated suspension of ice nucleating bacteria (INB) Pseudomonas Syringae ATCC 53543 and sucrose has been used. The sample was mixed until all sucrose crystals were dissolved, so that the final suspension contained 50 wt % sucrose. The suspension was placed in 20 ml vials at 2 g per vial. The vials were dried inside a vacuum chamber. The vials were sitting on the surface of a stainless steel shelf inside the chamber. The shelf temperature was controlled by circulating ethylene glycol/water antifreeze at a controlled temperature inside the shelf Before the vacuum was applied the shelf temperature was decreased to 5° C. Then, the hydrostatic pressure inside the chamber was decreased to 0.3 Torr. Under these conditions, the suspension boiled for 30 min. The temperature of the shelf was slowly (during 30 min) increased up to 25° C. Visually stable dry foams inside the vials under these experimental conditions were formed within 3 hours. After that the samples were kept under the vacuum at room temperature for one more day. Ice nucleating activity of preserved INB was measured after the sample rehydration with 10 ml of 0.01 M phosphate buffer. Ice nucleating activity was measured as a concentration of ice nucleating centers that can nucleate an ice crystal in a 10 $\mu$l buffer drop during 5 min. at−5° C. The results of the assay show ice nucleating activity in the preserved samples was equivalent to that observed in fresh controls.

(4) A concentrated INB suspension was frozen to −76° C. for future use. The frozen suspension (6 g) was thawed at 4° C. and mixed with 4 g of 9:1 sucrose: maltrin mixture. The sample was mixed until the sugars were completely dissolved, so that the final suspension contained 35 wt % sucrose and 4 wt % maltrin. The suspension was placed inside 20 ml vials at 2 g per vial. The vials were dried inside a vacuum chamber. The vials were sitting on the surface of stainless steel shelf inside the chamber. The shelf temperature was controlled by circulating ethylene glycol/water antifreeze at a controlled temperature inside the shelf. Before the vacuum was applied the shelf temperature was decreased to 5° C. The hydrostatic pressure inside the chamber was then decreased to 0.5 Torr. Under such conditions, the suspension boiled for 30 min. The temperature of the shelf was then slowly (during 30 min) increased up to 25° C. Visually, the formation of stable dry foams inside the vials under these conditions was completed within 2.5 hours. After removal of several vials, the temperature was increased to 50° C. and the remaining samples were kept under vacuum for 7 days.

Ice nucleating activity of preserved INB was measured after the sample was rehydrated with 10 ml of 0.01 M phosphate buffer. Ice nucleating activity was measured as a concentration of ice nucleating centers that nucleate an ice crystal in a 10 $\mu$l buffer drop during 5 min at −5° C.

The ice nucleating activity of the samples that had been removed from the vacuum chamber after drying at 25° C. was approximately 50% less than the initial activity of frozen-thawed INB. (The relative standard error in the measurement of ice nucleating activity is less than 20%), Because, it is known that freezing of INB does not significantly decrease ice nucleating activity, the 50% decrease of the activity observed in this experiment is probably because the additional freezing step increases sensitivity of INB to preservation by drying. At the same time, no additional decrease of the activity of the INB was observed after an additional 7 days drying at 50° C. under vacuum.

(5) When stable foams containing INB, prepared as above, were subjected to milling using a modified Virtis homogenizer, there was no loss of ice nucleating activity in the rehydrated powder, compared to the rehydrated foam.

(6) A 60 wt % sucrose solution (1 ml) was dried in 20 ml glass vials inside a vacuum chamber. The vials were sitting on the surface of a stainless steel shelf inside the chamber. The shelf temperature was controlled by circulating ethylene glycol/water antifreeze at a controlled temperature inside the shelf. The temperature of the shelf in this experiment was kept at 20° C. The hydrostatic pressure inside the chamber was kept equal to 0.3 Torr. Under such conditions the solution slowly boiled, forming a foam consisting of thin films containing concentrated sucrose in the amorphous state. It took 2 to 3 hours to form visually stable dry foams inside the vials under these experimental conditions.

(7) Freeze-dried samples of Urokinase were rehydrated with 2 ml of 40 wt % sucrose. The solutions were then transferred to 20 ml sterilized glass vials for future preservation by drying. Before drying, the vials were covered with gray slotted rubber stoppers. The vials were dried inside a vacuum chamber. The vials were sitting on the surface of a stainless steel shelf inside the chamber. The shelf temperature was controlled by circulating ethylene glycol/water antifreeze at a controlled temperature inside the shelf. Before the vacuum was applied the shelf temperature was decreased to 5° C. Then the hydrostatic pressure inside the chamber was decreased to 0.5 Torr. Under such conditions, the suspension boiled for 30 min. The temperature of the shelf was slowly increased up to 25° C. during 30 min. Visually, under these experimental conditions, stable dry foams were formed inside the vials within 3 hours. After an additional 12 hours of drying at room temperature, the temperature was increased to 45° C. for an additional 24 hours. After that the chamber was filled with dry $N_2$ gas, the rubber stoppers were pushed down and the vials were sealed with aluminum crimp seals.

The samples were assayed right after drying and after 30 days of storage at 40° C. After drying the Urokinase, activity was 93% of the initial activity. This decrease was associated with the loss of Urokinase during transfer from initial vials to the vials at which the Urokinase was dried. After 30 days of storage at 40° C. the activity was 90%. In other words, no additional significant decrease of Urokinase activity was observed during a month of storage at 40° C.

(8) Freeze-dried samples of Amphotericin B were rehydrated with 5 ml 40 wt % sucrose per vial. Then the solutions were transferred into 50 ml sterilized glass vials for future preservation by drying. Before drying, the vials were covered with gray butyl slotted rubber stoppers. The vials were dried inside a vacuum chamber. The vials were placed on the surface of a stainless steel shelf inside the chamber. The shelf temperature was controlled by circulating ethylene glycol/water antifreeze at a controlled temperature inside the shelf. Before the vacuum was applied the shelf temperature was decreased to 5° C. The hydrostatic pressure inside the chamber was decreased to 0.5 Torr. Under such conditions the suspension boiled for 30 min. The temperature of the shelf was then slowly (during 30 min) increased to 25° C. Visually, stable dry foams were formed inside the vials under these experimental conditions within 3 hours. After an additional 12 hours of drying at room temperature, the chamber was filled with the dry $N_2$ gas and the rubber stoppers in a portion of the vials were pushed down. The vials were removed from the chamber and subsequently sealed with aluminum crimped seal. The samples were assayed right after drying and after 30 days of storage at 27.5° and 40° C. The results are shown in Table 1, together with the results obtained in the next experiment.

Another set of freeze-dried samples of Amphotericin B was rehydrated with 5 ml 40 wt % sucrose per vial. The solutions were then transferred into sterilized glass vials for future preservation by drying similar to that described above with additional drying at 4520 C. for additional 24 hours. After that, the chamber was filled again with the dry $N_2$ gas, the rubber stoppers were pushed down and the vials were sealed. The samples were assayed right after drying and after 30 day of storage at 27.5° and 40° C. The results are shown in Table 1.

TABLE 1

| | Potency of Amphotericin (%) | | |
|---|---|---|---|
| | After drying | After 30 days at 27.5° C. | After 30 days at 40° C. |
| Td = 25° C. | 108 | 114 | 95 |
| Td = 45° C. | 103 | 102 | 104 |
| Control | 126 | N/A | N/A |

Where Td is the maximum temperature during drying

The decrease of Amphotericin activity right after drying was associated with the loss of Amphotericin during transformation from initial vials to the vials at which the Amphotericin was dried. The results of the assay (Table 1) suggested that the loss of potency was only detected in those samples dried at the lower temperature (25° C.) and subsequently stored at 40° C.

(9) A 1.5 ml tube containing a frozen (−76° C.) suspension of *E. coli* (XL10-GOLD) from Stratagene was thawed in an ice bath. A 100 $\mu$l aliquot was transferred to 50 ml of NZYM (Casein digest yeast extract medium) broth and incubated at 37° C. on an orbital shaker overnight. After 14 hours of growth, 10 ml of this growth culture was inoculated into 100 ml of sterile NZYM broth to continue the culture growth at 37° C. During the culture growth the optical density (OD@620 nm) was measured every hour to determine the end of logarithmic bacteria growth. When the transition phase was reached (OD=1 to 1.06) the cells were ready to be harvested. The culture medium (5 ml) was pipetted into a centrifuge tube and centrifuged for 10 min. The supernatant was then poured off and the weight of the pellets was measured to determine the approximate concentration of the cells.

The cells were resuspended with 5 ml of NZYM broth or preservation solution consisting of 25% sucrose and 25% fructose in MRS broth. The cells resuspended with NZYM broth were used as a control. The cells suspended in 25% sucrose and 25% fructose in MRS broth (1 ml) were placed in 20 ml glass vials and dried under vacuum similar to the DNM were dried in the Example #2. After that, the samples were kept under vacuum up to 24 days at room temperature. Dried samples were assayed at selected time intervals. The survival of the preserved cells was measured after rehydration with 0.1% peptone solution in water at room temperature. To determine concentration of viable cells the suspensions were pour plated in Petri dishes at the appropriate dilution on L B Miller agar followed by incubation at 37° C. for 36–48 hours. Approximately 25±10% of control cells survived after drying and one day of storage under vacuum. Moreover, the portion of surviving cells did not decrease during the subsequent 24 days of storage under vacuum at room temperature.

Stability Drying/Vitrification—The mechanically stable foams formed during primary drying, may optionally undergo secondary or “stability” drying at increased temperatures. Since Tg is dependent on the water content of the sample and since Tg increases with increased dehydration, different stability drying protocols may be applied depending on the desired storage temperature, to generate a Tg consistent with vitrification upon cooling to that storage temperature. However, because dehydration of materials is practically impossible once they have entered the glass state, the key to vitrification according to the present invention, where ambient storage temperatures may be desired, is to conduct the stability drying at a temperature significantly higher than the ambient temperature.

Ultimate storage temperatures are preferably within the range of 0°–70° C. More preferably, common storage temperature selections are greater than or equal to 0°, 4°, 20°, 40°, and 50° C. In some cases, where refrigerated storage may be preferred, stability drying could be carried out at room temperature followed by cooling to the storage temperature or below. In other instances, however, where stability at room temperature is desired, dehydration at a temperature above room temperature should be employed, followed by cooling to room temperature.

For any given specimen to be preserved, the nature and stability characteristics of the specimen will determine the maximum temperature it can withstand during the primary drying step. In the case of enzyme preservation, it was shown that after primary drying at room temperature the stability drying temperature may be increased up to 50° C. without loss of enzymatic activity. Then, the dehydration process can be continued during stability drying at higher temperature. Thus, by continuous or step-wise increases in the dehydration temperature, labile proteins can be placed in a state of thermal stability it temperatures well above their denaturation temperature.

In addition to conducting the stability drying at a temperature above the selected storage temperature, it is critical that this drying is carried out for a period of time sufficient to actually raise Tg above the storage temperature. Based on empirical results obtained with dried 10 ul drops of 15% sucrose+15% raffinose solution, it was demonstrated that more than 12 hours of stability drying at temperatures above 70° C. was required to raise Tg to above 25° C. Primary drying in these experiments was for 12 hours at room temperature (20° C.). The results suggest that extended stability drying times (more than 12 hours at 70° C. and more than 36 hours at 50° C.) may be needed to effect increases in Tg over room temperature. For some biological materials which are not heat labile, primary drying at higher temperatures, would reduce the stability drying time at elevated temperatures needed to increase Tg to above the selected storage temperature.

In one embodiment of the present invention, the foam is cooled from stability drying down to the milling temperature, milled, and then the powder is subjected to fisher drying either under vacuum or at atmospheric pressure. The subsequent drying temperature may be in the range of about 0° to 100° C. Such drying may be continued until the glass transition temperature is raised above a selected storage temperature within in the range of about 0° to 70° C.

To ensure that the Tg is actually greater than the storage temperature, at least two methods are known for estimating Tg by thermal analysis. Differential scanning calorimetry (DSC) is the most commonly used technique. However, the Inventor has found that DSC may be unreliable for measuring Tg in samples that contain polymers. Alternatively, Thermally Stimulated Polarization Current (TSPC) methods are specifically adapted for analysis of polymers. The TSPC method is preferred because it is reliable for all samples, although it requires slightly larger sample volumes.

Formation of a Uniform Powder—Regardless of the means selected for crushing the stable foam to a powder, the apparatus of the present invention preferably incorporates such crushing means within the same chamber, cylinder, or vessel in which the primary and optional stability drying step(s) are accomplished. Indeed, one of the advantages of the present invention is the integration of functions, previously carried out by separate pieces of equipment. Thus, a crushing means is preferably housed in the processing chamber and operated when at least one of the preservation step(s) have been completed.

Crushing means in accordance with the present invention includes conventional mills, homogenizers and sonicators, as well as other means for reducing the stable foam to a powder. These other means may include the physical deformation of a second container placed inside the drying chamber. The second chamber may be semirigid, wherein the foam is powdered by physical blows to the container or may be flexible, like a bag, wherein the foam is powdered by crushing or other physical deformation. Alternatively, preservation may take place within grid cells in a partitioned tray, wherein the foam may be scraped from the grid and crushed. The various crushing means are described in greater detail below.

A. Conventional Milling—Conventional milling methods and components may be used in accordance with the present invention. These include without limitation: brush mills; rotating blade mills as described in U.S. Pat. No. 5,352,471, incorporated herein by reference; pulverizing mills as described in U.S. Pat. No. 4,651,934, incorporated herein by reference; rotary attrition mills described in U.S. Pat. No. 4,404,346, incorporated herein by reference; jet mills, for example, of the type of the spiral or counter-pipe mills (C F Winnacker, Kucher; *Chemische Technologie,* 4th Edition, Volume 1, p.91–93, 1984) as described and improved in U.S. Pat. No. 4,917,309, incorporated herein by reference; incremental cutting action mills, for example, a COMITROL® 1700 Mill, as described in U.S. Pat. No. 5,520,932, incorporated herein by reference; ball mills; hammer mills (e.g. MIKROPULVERIZER®); rotary tubular mills containing impact resistant metal balls, metal cylinder or bars or stones, for example, the micronizing mill described in U.S. Pat. No. 5,174,512, incorporated herein by reference; homogenizers; sonicators; and mills containing wires, like a weed-whacker; and any other milling means known in the art. The differences and advantages of the various types of mills, grinders and crushing mechanisms are well known to those of ordinary skill in pharmaceutical manufacturing techniques B. Deformable Container—There are a number of alternative approaches that can be taken to implement the concept of drying and reducing to a powder in the same drying chamber. A variation from conventional milling uses a second container placed inside the drying chamber. This second container would serve as the holder of the process fluid that is to be preserved via foam formation. The container would be placed in the chamber and filled with the preservative solution. This filling could be accomplished via a separate filling tube. Subsequent to the completion of preservation by foam formation, this same container could be sealed and withdrawn from the drying chamber and serve as either a final container or an intermediate container for further processing. Sealing could be accomplished via a simple capping device for semirigid containers or via heat sealing for flexible containers. In addition, if the container is semirigid, the mechanically stable foam contained within may be broken up in a kind of coarse milling, via a series of impacts of the container wall to a hard inflexible surface, or vice versa. If the container is flexible, as with a gas-permeable Lyoguard® bag, the foam contained within it may be coarsely milled by crushing the bag, using a relatively weak force. This could be accomplished with a simple roller device. Once coarsely broken up, the resulting particles may be either considered to be in finished form or, depending upon end use requirements, processed further by transferring to a milling machine. Since at this point the material would be in particle form, this transfer would be effected easily by gravity or vacuum devices commonly used in powder handling systems. The final milling would be performed by commercially available milling equipment and conducted in such a way as to mill the material to a particular particle size distribution as dictated by material final specifications. A Quadro Comil®, for example, would be suitable for this purpose.

Since the secondary container would be in a vacuum environment during preservation by foam formation, the transfer of heat to the preservation solution inside could be slow and difficult to control. This limitation could be overcome by using the concept of inductive heating. An induction coil wound around the exterior of the chamber would provide the heating source by inducing molecular motion in ionic species in the preserving solution. Alternatively, a bag holding device, termed a cassette, which would slide into and out of the drying chamber to provide for easier loading and unloading of the product could also serve as the device which would support the induction coil. An embodiment of the apparatus of the present invention is illustrated in FIG. 1. The condenser 10 is connected to the drying chamber 14, which has a heater 12. A cassette 16 is adapted to fit within the drying chamber and to hold the deformable container 24. The apparatus also comprises a refrigerator system 18 a vacuum pump 20 and a rotation drive motor 22. Alternatively, the cassette could serve as the housing for more traditional heat transfer systems such as electrical resistance heating and recirculatory fluid heating. In order to provide for more uniform processing of the preservation solution, the cassette holding the container could also be made to rotate.

The concept of a second container provides a number of advantages beyond those already identified above. In particular for aseptic processing, the filling tube, chamber and the container could be pre-sterilized by commonly accepted practice (e.g., irradiation, vaporous hydrogen peroxide (VHP), steam, etc., depending on the materials of construction of the respective items). This approach, coupled with the sealing devices described above, provides for a barrier-type of processing, thus effectively isolating the operator and product from each other during the course of preservation by foam formation. This is highly desirable for handling biological and toxic materials. The use of isolation or barrier technology is becoming the standard design approach for processing such materials in the pharmaceutical industry.

A number of feasibility experiments have been conducted which have demonstrated proof-of-concept. Working examples and the results obtained using a deformable container are presented below.

(1) In the first test, the equipment set-up consisted of a 4½ inch internal diameter glass tube connected to a standard Virtis SL600 Unitop condenser section and heated via two laboratory style hot plates from Corning. The opposite end of the glass tube was closed. A 200 ml solution of sucrose 50% w/w/ in de-ionized water was introduced to a 2L PET beverage bottle, commonly used for soft drinks. This would qualify as a semi-rigid container. The bottle was placed in the tube and the sucrose solution was preserved by foam formation. After mechanically stable foam was formed, the bottle containing the foam was held overnight at 0.3 Torr and 25° C. The next morning the vacuum was broken with air. Total process time was 23 hours. Immediately following tube disassembly, the bottle was removed from the tube and purged with dry nitrogen for approximately one minute. The bottle was capped with the accompanying plastic screw top. The foam appeared to completely fill the bottle. Slight pressure applied by hand on the outside of the bottle showed the foam to be extremely brittle. Next the bottle was struck against the laboratory counter about 8–10 times with light-moderate force. All of the foam inside broke apart into discreet particles with the visual and flow characteristics of sand. A small amount of material remained adhering to the bottle interior. The glass transition temperature of the coarse particulate material was 18° C.

(2) In a second test, the glass tube used in the first test was replaced with a jacketed glass tube. The jacket was filled with water and connected to a recirculating heater bath. The bottle used previously was replaced with a 1-gallon capacity polyethylene plastic storage bag, commonly available in supermarkets. This would qualify as a flexible container. The bag was taped in place to a plastic holder to keep the bag open. The bag was filled with 150 ml of 50% w/w sucrose in de-ionized water. Primary foam drying was essentially completed 90 minutes later and the heating source switched to hot plates. Conditions at that point were 31° C. and 0.15 Torr. The foam was then held overnight. In the morning the vacuum was broken with dry nitrogen, the bag removed, purged with nitrogen for approximately 1 minute and then placed inside a Zip-Loc® 1-gallon plastic storage bag. Total process time was 71 hours. Gently crushing the bag by hand immediately reduced the foam to particles much like those produced in the bottle previously. The glass transition temperature of the resulting particles was 18.33° C.

(3) In a third test, the previous style bag was replaced with a longer, larger bag obtained from the bags used to package Petri dishes as supplied by VWR (100x15 mm size dishes). A 300 ml volume of sucrose solution, again 50% w/w in deionized water, was filled in the larger bag. After approximately 3 hours of primary foam drying, the heat was turned off on the circulating bath and heat supplied via the two hot plates. The next morning the hot plates were turned off (T=30° C, P=0.8 Torr) and the circulating bath set to 50° C. After about 7 hours the system temperature and pressure were 55° C. and 0.2 Torr, respectively. Total process time was 23½ hours. The system vacuum was broken with dry nitrogen, the bag removed, transferred to a 1-gallon Zip-Loc® bag and crushed gently. As before, all of the foam easily reduced to the particles like those seen previously. The glass transition temperature was 33.3° C.

(4) The bacterial strain *Lactobacillus acidophilus* was grown in a two liter capacity fermenter using a standard protocol specific to the species. The fermenter cell population was counted at $8.1\pm0.73\times10^8$. The cells were harvested by centrifugation, resulting in 200 ml of cell concentrate with a population of $7.83\pm0.75\times10^9$. The cell concentrate was diluted in preservation solution consisting of 800 ml of 40% sucrose, 10% methyl α-D glucopyranoside dissolved in 50% buffer (w/w). The resultant mixture was filled into a polyethylene Petri dish bag at 300 ml. The remainder was reserved for another use. The empty polyethylene bag was attached to a holding device located inside a 4½x19 inch, cylindrical glass chamber supported by an aluminum frame. This glass chamber served as the bulk drying chamber for preservation by foam formation. The test solution was filled into the polyethylene bag with the aid of a length of silicone tubing. The glass chamber was also fitted with an external glass water jacket along the entire tube length. The jacket was coupled to a recirculating, temperature controlled water bath. The water jacket served as the heating source for the process. The glass chamber was connected at the discharge end to the condenser of a lyophilizer. At the conclusion of the preservation by foam formation process, the system vacuum was broken with dry nitrogen. The bag was removed and examined. Dry, mechanically stable, brittle foam had clearly been produced. The material was gently crushed into particles with the consistency of sand, using light hand pressure. The bag was cut open and the contents transferred to a clean container. The container was sampled in triplicate. The container was then purged with dry nitrogen and sealed. The samples were cultured and cell populations compared to control cultures of 1 ml of dried *Lactobacillus acidophilus* foam-dried in 10 ml vials by the same process. Results that clearly demonstrate survival of the test bacterial strain are summarized below:

| Sample Origin | Plate Count Mean | Plate Count Std. Dev. | Mass Assayed (g) | Volume Diluent (ml) | Activity Cell/g | Average per Sample | % Viable vs. Vial Control |
|---|---|---|---|---|---|---|---|
| Bag A | 1.21E+09 | 0.91E+07 | 0.2415 | 2.4 | 1.21E+09 | 1.12E+09 | 92.50 |
| Bag A | 1.09E+09 | 1.05E+08 | 0.3366 | 3.4 | 1.09E+09 | | 83.10 |
| Bag A | 1.07E+09 | 1.07E+08 | 0.1848 | 1.8 | 1.07E+09 | | 81.32 |

Gas-Permeable Bag—A product (now called Lyoguard®) developed by W. L. Gore for bulk lyophilization in an aseptic manner was also tested for its utility as an insert, deformable container in the process of preservation by foam formation. The Lyoguard® lyophilization bag was a heat sealable flexible bag consisting of one side that was a plastic that was not permeable to water vapor and another side consisting of a Gore-Tex® membrane. This membrane is an expanded polytetrafluoroethylene (PTFE), nominally 0.2 micron pore size, hydrophobic and not permeable to liquid water, but permeable to water vapor.

Because the Lyoguard® bag can pass water vapor while still preventing product in the liquid state from penetrating the membrane and leaking out, it provided an ideal way to process pharmaceutical products which in general require sterility. The basic method could also be applied to animal health products, probiotics, food, etc. In short, any product for which closed container processing might have an advantage in the areas of sterility, ease of handling, isolation of pathogens (e.g., bacteria and viruses) from the operators and extraneous particle contamination control could potentially benefit from application of the Lyoguard® bag to preservation by foam formation. In addition the flexible nature of the bag enhances the contact of the bag with the dryer shelf. Since the shelf is the heat transfer surface in a conventional freeze dryer, heat transfer should be optimal when conducting preservation by foam formation with the Lyoguard® bag. This could lead to faster drying cycles.

A series of experiments were initiated to investigate the possibilities of using the Lyoguard® Gore-Tex bag for preservation by foam formation. A 50% solution w/w with de-ionized water served as the testing media. A volume of 200 ml was filled into a 10×14 inch Lyoguard® bag. The bag was then heat-sealed using a commercially available heat-sealing device. Next the bag was placed on the one of the 3 shelves of the Virtis Genesis® lyophilizer which UPT has had custom-modified for preservation by foam formation. The drying process was conducted. Boiling and eventually foam formation were observed through the semitransparent lower impermeable membrane of the bag as drying proceeded. After overnight drying at 40° C., the bag was removed from the lyophilizer and examined. Mechanically stable foam appeared to have formed. This dried foam was brittle and easily crushed into small particles in the bag without opening the bag. This indicated that the bag could also function as a container far coarse milling of the foam product. Within approximately 30 minutes the bag was opened and about 1 L of water was added to observe the reconstitution character of the dried particles. Most of the particulate easily dissolved in less than 10 seconds. Subsequent test protocols involving altered pressure and temperature ramps and fills ranging from 200 to 400 ml in the 10×14 inch bag suggested that about 300 ml was the optimal fill level. At the completion of a typical run the appearance of the bag shows complete formation of foam and all of the material in the bag redissolves easily.

Bulk lyophilization of industrial enzymes, foods and pharmaceuticals is commonly done by utilizing stainless steel trays, which are placed on the temperature controlled shelves of the lyophilizer. The trays are typically filled in an appropriate environment for the particular product of interest and transported to the freeze dryer, whereupon they are loaded into the dryer and the lyophilization cycle is run. Tray dimensions and capacity are largely determined by the shelf area of the lyophilizer, the allowable fill height for the product and the material handling characteristics desired. For preservation by foam formation, the basic operation would be the same. Product is prepared according to the previous examples, poured into standard lyophilization trays and preserved by foam formation in a machine configured to meet the required conditions. The tray could be constructed of any material that would allow the transfer of heat from the product shelf to the product contained within the tray. Examples of suitable materials are stainless steels, coated steels, non-ferrous alloys such as aluminum and titanium and plastics such as polypropylene, polyethylene and the like. It is recognized that plastics will transfer heat less efficiently, but may have other offsetting advantages.

Because of certain aspects of preservation by foam formation, a number of innovations described herein are necessary to the typical lyophilization tray in order for it to perform properly in the production of a mechanically stable, dry foam. In a preferred embodiment the tray would be fitted with a grid structure located in the internal space defined by the tray bottom and sides. This grid structure would essentially divide the area of the tray into a series of cells of equal or unequal area such that the entire tray would be sectioned into smaller units. The function of the grid would be to reduce the area available for expansion of the foam during preservation by foam formation, thereby containing foam bubbles inside the area of each grid. This effectively reduces the height to which a foam structure can grow, thus minimizing the chance that the growing foam will contact the dryer shelf or other dryer surface immediately above the foam and/or overflow out of the tray. The grid structure can take any geometric shape that will fit inside the tray. A square pattern such as that used to separate vials in shipping containers would be an example. Grid wall height should be at least half the height of the tray side to preclude the interconnection of foam bubbles with adjacent bubbles as the foaming process proceeds.

In another embodiment the tray would have a cover placed over the entire area defined by the tray bottom. This cover would be located in such as way as to permit the escape of water vapor during preservation by foam formation. The gap between the cover edge and top of the sides of the tray should be ¼ inch or less. Although gaps of larger dimensions would certainly work, it is a desideratum to minimize the shelf to shelf spacing in order to maximize the volume available for production. The tray cover would be supported by any means available to effect such support and provide the clearance necessary between the top of the tray sides and the cover bottom edge. Auxiliary posts, integral cover tabs or spacers made of any of the above materials or any similar method would accomplish the required spacing. These tray drying methods could be applied to animal health products, probiotics, food, industrial enzymes etc.

Bulk Drying in Trays—A series of experiments was conducted to investigate the feasibility of bulk drying in trays using a freeze dryer, modified for preservation by foam formation. In the first experiment, 400 ml of test solution, consisting of 50% sucrose w/w in deionized water, was filled into a stainless steel tray measuring 9½x19 ½x1¼ inches. The tray was placed on the middle shelf of a 3-shelf dryer. The material was then dried in accordance with the present invention. This test showed that although the tray could work as a bulk foaming container, there were problems both in containing the foam and in splashing of liquid onto adjoining surfaces during the boiling process. It was initially believed that both of these problems were serious enough to preclude the use of trays for preservation by foam formation. However, close observation showed that the foam bubbles appeared to bridge across the whole area of the tray. Consequently, it was theorized that reducing this available area would prevent the foam bubbles from growing uncontrollably.

An insert consisting of a plastic-coated cardboard material in a 1 7/16x1 7/16 inch grid, which had been used to separate 20 ml vials in their shipping cartons, was cut to fit inside the stainless steel tray used in the previous test. A series of experiments were conducted using the grid insert. These tests showed that the foam could be produced much more controllably and the splattering outside of the tray reduced considerably when the grid was used. However, the test material showed a pronounced tendency to stick to the tray, making removal difficult after the cycle was completed. Coating the stainless steel surface with a non-stock coating such as polytetrafluoroethylene (PTFE) could provide a solution to that problem.

In order to test this idea, it was decided to explore the use of plastic trays. A 9½x19½x2½ inch tray was made of high-density polyethylene (HDPE). A removable HDPE insert having a 6 cell ×12 cell grid and a HDPE cover was also fabricated. In another series of experiments, the recovery from the tray clearly improved. The resulting foam also hydrated easily and quickly when reconstituted. Use of the cover led to control of splattering. In addition, cell-to-cell foam uniformity was also improved within the tray. Bulk drying in trays with grids may require the removal of the material from individual grid cells on the tray. One means of facilitating this would be to fabricate a device to manually, semiautomatically or automatically hold the tray and scrape the contents out of the tray interior. This could be accomplished by separately gripping the tray and tray insert, pulling them apart and then drawing a close clearance, blade-type scraper across the exposed tray interior. The insert could be scraped clean via the application of mechanical fingers sized for close clearance to the grid cell dimensions. These fingers would be forced through the grid cells, pushing the material out of the cells onto a surface that could be further scraped clean into a collection container.

Figure 2:
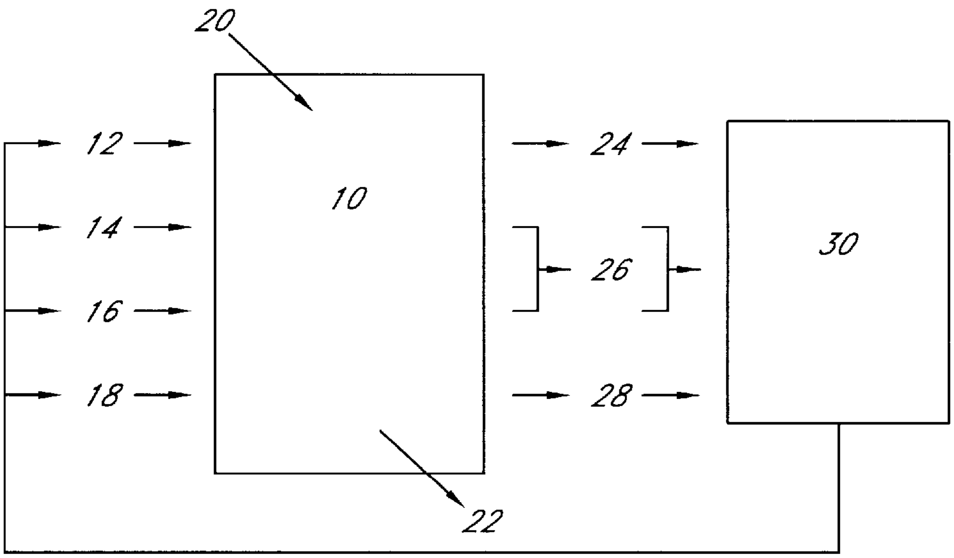
FIG. 2 is a flow diagram depicting an automated embodiment of the integrated drying-milling apparatus of the present invention.

Processing Chamber—The processing operations disclosed herein, comprising initial concentration, primary foam-drying, stability drying/vitrification, and subsequent milling are preferably conducted in a closed apparatus using barrier technology. In its simplest embodiment, the inventive apparatus may be a novel combination of a chamber having a heater and a cooler and a thermostat for regulating chamber temperature, a vacuum pump and a pressure-release valve for regulating chamber pressure, and a means for crushing a mechanically-stable porous foam. The apparatus may optionally be provided with a means for rotating the chamber during processing, such as a motor with a direct or belt drive mechanism, as is well known in the art. Referring to FIG. 2, the apparatus preferably includes detection means for monitoring temperature 26, pressure 24 and milling 28 within the chamber 10. Means for increasing 14 or decreasing 16 the temperature, and controlling pressure 12 and milling 18 parameters may be actuated manually, by the operator, or preferably, by a programmable computer 30 adapted to monitor temperature 26, pressure 24, and milling 28 data (e.g. rpm or cycles per minute, etc.), integrate that information, and initiate responsive actions upon the various means for regulating temperature, pressure and milling.

The processing chamber 10 preferably has separate inlet 20 and outlet 22 ports for introduction of the biological materials and dispensing of the milled product, respectively. The apparatus of the present invention includes means for regulating chamber temperature and pressure, as well as means for regulating milling. Means for regulating temperature may include a heater and a refrigerator/freezer and a thermostat, which together are capable of producing chamber temperatures in a range from about −70° to 100° C. during the various processing operations. Optionally, the heater may also be able to provide intra-chamber temperatures for sterilization in the range of about 100° to 300° C. Means for regulating chamber pressure comprise a vacuum pump, optionally fitted with a condenser with a pressure-release or bleed valve that may be able to produce chamber vacuums in the range from about 0–500 Torr. More preferably, the vacuum pump may produce chamber pressures in the range of about 0–24 Torr (high vacuum) to about 0.1–0.9 atm (low vacuum). A mill controller may provide external means for controlling operation of the mill; the milling elements (e.g. brushes or blades) are located inside the chamber. In addition, preferred features of the apparatus may include a temperature sensor, pressure sensor, and possibly a detector for mill operation (e.g. tachometer).

Although the apparatus of the present invention need not necessarily incorporate a microprocessor or utilize computer-actuated control means, the use of a programmable computer to integrate the temperature, pressure and milling data, generate real-time control signals, and execute step-wise or simultaneous gradients of both temperature and pressure in accordance with programmed instructions allows automated implementation of a novel two-dimensional temperature and vacuum protocol for drying.

A variety of processing chamber materials and sizes are encompassed within the present disclosure. Indeed, the apparatus may be produced with smaller, analytical sized chambers, as well as larger, industrial scale chambers. Any materials may be employed in making the chamber as long as they are stable at the indicated temperature and pressure ranges, and compatible with the sensitive biological solutions and suspensions. Exemplary materials for construction of the processing chamber include stainless steel, glass, and Plexiglas. Further, the chamber can be sterilized by conventional means. In one embodiment, the unit's heating means may be operated between sample runs at temperatures sufficient to sterilize the chamber and the enclosed milling means. Moreover, the integrated design preferably employs barrier technology, wherein no sample manipulation is required once it has been introduced into the closed system; thus, maintaining optimal product quality and sterility.

Another embodiment of the present invention includes the integrated functions of drying, milling and formulating a mixture of dry powders to form a "cereal" for various applications. For example, the bacterial strain *Lactobacillus acidophilus* is grown in a two liter capacity fermenter using a standard protocol specific to the species. The fermenter cell population is harvested by centrifugation and the cell concentrate is diluted in preservation solution consisting of 800 ml of 40% sucrose, 10% methyl α-D glucopyranoside dissolved in 50% buffer (w/w). The resultant mixture is foam-dried as described above in a deformable container. At the conclusion of the preservation process, the system vacuum is broken with dry nitrogen. The deformable container is sealed, removed from the drying chamber and the porous foam is gently crushed into particles with the consistency of sand, using light hand pressure.

A solution of 5% Vitamin C in the same preservation solution as the Lactobacillus above is foam-dried in a deformable container. The deformable container is sealed and the porous foam is crushed. Subsequently, the probiotic Lactobacillus powder can then be mixed with the Vitamin C powder using conventional powder handling equipment adapted for maintaining sterility to form a complex cereal having unique properties related to the probiotic and vitamin components. Such formulations may be prepared by mixing a variety of different biological and pharmacological powdered ingredients, such as mixing different vaccines or different antigens.

Powders representing a single component or formulations can then be used to prepare pharmaceutical compositions. For example, the materials can be pressed into tablets, which provide quick dissolvable solid dose preparations.

Although the invention has been described in detail for the purposes of illustration it is understood that such detail is solely for that purpose, and variations can be made therein by those skilled in the art without departing from the spirit and scope of the invention which is defined by the following claims.

What is claimed is:

1. A barrier method for preserving a biological solution or suspension as a powder, comprising:

drying a volume of at least 1 ml of the biological solution or suspension in a chamber by boiling under vacuum at a temperature in a range of −15° to 70° C. to form a mechanically-stable foam; and crushing the mechanically-stable foam to form a powder.

2. The method of claim 1, wherein said vacuum is between 0 and 24 Torr.

3. The method of claim 1, wherein said vacuum is below about 4 Torr.

4. The method of claim 1, wherein prior to said drying step, a vacuum is applied to said biological solution or suspension to purge dissolved gases.

5. The method of claim 1, wherein said biological solution or suspension is combined with a protectant prior to said drying step.

6. The method of claim 5, wherein said protectant is selected from the group consisting of sugars, polyols and polymers.

7. The method of claim 6, wherein said protectant further comprises a mixture comprising a monosaccharide, a disaccharide, an oligosaccharide and a polymer.

8. The method of claim 6, wherein said sugar is a non-reducing derivative of a monosaccharide.

9. The method of claim 8, wherein said non-reducing derivative is prepared from monosaccharides having at least one reducing group, wherein the at least one reducing group is modifying by methylation, ethylation, or chlorination.

10. The method of claim 1, wherein prior to said drying step, said biological solution or suspension is combined with a surfactant.

11. The method of claim 1, wherein prior to said crushing step, the foam is further dried under conditions sufficient to increase its stability at a desired storage temperature.

12. The method of claim 1, wherein prior to said crushing step, the foam is further dried at a temperature above a glass transition temperature for a period of time long enough to increase the glass transition temperature above a desired storage temperature, wherein the glass transition temperature is measured by a thermally stimulated polarization current method.

13. The method of claim 1, wherein the powder is further dried under conditions sufficient to increase its stability at a desired storage temperature.

14. The method of claim 1, wherein the powder is further dried under conditions sufficient to increase its glass transition temperature above a desired storage temperature.

15. The method of claim 1, wherein a means for crushing the foam is incorporated into the chamber.

16. The method of claim 15, wherein said crushing means comprises a mill selected from the group consisting of a brush mill, a rotating blade mill, a pulverizing mill, a rotary attrition mill, a jet mill, an incremental cutting action mill, a ball mill, a hammer mill, a rotary tubular mill, a homogenizer, and a sonicator.

17. The method of claim 15, wherein said crushing means comprises a deformable container inside the chamber, wherein said drying step is conducted in the deformable container.

18. The method of claim 17, wherein said crushing step is accomplished by mechanically deforming the deformable container.

19. The method of claim 18, wherein the deformable container is sealed prior to deforming the container.

20. The method of claim 17, wherein the deformable container is gas-permeable to allow drying of said biological solution or suspension.

21. The method of claim 17, wherein the deformable container is semirigid.

22. The method of claim 1, wherein said drying step is conducted on a tray inside the chamber.

23. The method of claim 22, wherein the tray is subdivided by a grid.

24. The method of claim 1, further comprising the step of rotating the chamber during at least one of said steps of drying and crushing.

25. The method of claim 1, wherein the chamber is sized to allow drying and crushing of a volume of biological solution or suspension of at least one liter.

26. The method of claim 1, wherein the chamber is sized to allow drying and crushing of a volume of biological solution or suspension of at least ten liters.

27. The method of claim 1, wherein the chamber is sized to allow drying and crushing of a volume of biological solution or suspension of at least one hundred liters.

28. A barrier method for preparing a powdered formulation of preserved biological materials, comprising:

drying at least two solutions or suspensions containing a biological material by boiling under vacuum at a temperature less than 100° C. to form at least two mechanically-stable foams;

crushing the mechanically-stable foams to form at least two powders; and mixing the powders containing the biological materials to form a powdered formulation, wherein the biological materials are barrier-protected against exposure to an outside environment throughout the drying, crushing and mixing steps.

29. An integrated apparatus for drying and crushing a biological solution or suspension, comprising a chamber having a heater and a cooler and a thermostat for regulating chamber temperature, and a vacuum pump and a pressure release valve for regulating chamber pressure, wherein the chamber temperature and pressure can be regulated to cause the biological solution or suspension to boil to form a mechanically-stable porous foam, and a means for crushing the mechanically-stable porous foam.

30. The apparatus of claim 29, wherein the heater, cooler and thermostat for regulating chamber temperature are capable of producing a chamber temperature within a range of about −70° to 300° C.

31. The apparatus of claim 29, wherein the heater, cooler and thermostat for regulating temperature are capable of producing a chamber temperature within a range of about −70° to 100° C.

32. The apparatus of claim 29, wherein the vacuum pump and pressure-release valve for regulating pressure are capable of producing a chamber pressure within a range of about 0 to about 500 Torr.

33. The apparatus of claim 29, wherein the vacuum pump and pressure-release valve for regulating pressure are capable of producing a chamber pressure within a range of about 0 to about 24 Torr.

34. The apparatus of claim 29 further comprising a motor for rotating the chamber.

35. The apparatus of claim 29, wherein said means for crushing comprises a mill inside the chamber or a deformable container inside the chamber.

36. The apparatus of claim 35, wherein said mill is selected from the group consisting of a brush mill, a rotating blade mill, a pulverizing mill, a rotary attrition mill, a jet mill, an incremental cutting action mill, a ball mill, a hammer mill, a rotary tubular mill, a homogenizer, and a sonicator.

37. The apparatus of claim 35, wherein the deformable container is a bag.

38. The apparatus of claim 35, further comprising a cassette adapted to support said deformable container within the chamber.

39. The apparatus of claim 38, wherein the cassette includes elements for facilitating heat transfer.

40. The apparatus of claim 29 further comprising a sensor for detecting chamber temperature.

41. The apparatus of claim 29 further comprising a sensor for detecting chamber pressure.

42. The apparatus of claim 29 further comprising a sensor for monitoring said crushing means.

43. The apparatus of claim 29 further comprising a programmable computer adapted to monitor chamber temperature and chamber pressure, said computer further being adapted to control chamber temperature and chamber pressure.

44. The apparatus of claim 43, wherein said computer is further adapted to control said crushing means.

45. The apparatus of claim 29, further comprising a tray in the chamber.

46. The apparatus of claim 45, wherein the tray is subdivided by a grid.

47. The apparatus of claim 46, wherein the tray further comprises a cover for reducing splatter.

* * * * *